(12) United States Patent
Bhat et al.

(10) Patent No.: US 6,911,562 B2
(45) Date of Patent: Jun. 28, 2005

(54) PROCESS FOR THE PREPARATION OF A COSMETIC ACTIVE

(75) Inventors: Ramachandra Bhat, Mumbai (IN); Vinodkumar Ramniranjan Dhanuka, Mumbai (IN); Bijan Harichian, Edgewater, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/887,396

(22) Filed: Jul. 8, 2004

(65) Prior Publication Data

US 2005/0054884 A1 Mar. 10, 2005

(30) Foreign Application Priority Data

Jul. 8, 2003 (IN) ................................. 689/03
Sep. 24, 2003 (GB) ............................. 0322300

(51) Int. Cl.[7] ............................................. C07C 37/00
(52) U.S. Cl. ....................... 568/772; 568/766
(58) Field of Search .................. 568/766, 772

(56) References Cited

U.S. PATENT DOCUMENTS 4,419,529 A * 12/1983 Steinmetz ................... 568/772

FOREIGN PATENT DOCUMENTS

DE 489 117 1/1930

OTHER PUBLICATIONS

GB Search Report, GB 0322300.5, dated Jan. 22, 2004—3 pp.
J. Med. Chem., 1986, 29(5), 606–11 ., (Elsohly).
J. Am. Chem. Soc., 1939, 61, 249–54, (Hurd).
Australian Journal of Chemistry, 1969, 22(3), 601–5, (Bell).
J. Am. Chem. Soc., 1930, 52, 4866–82, (Brewster).
Rec. trav. Chim., 1931, 50, 848–50, (Cox).
Synthetic Communications, 1985, 15(14), 1315–24, (Elliger).
Tr. Tallin. Politekhn, In–ta. 1983, (543), 78–83, no translation.
Zymalkowski, et al., "Die Reduktion von beta–benzoyl–propionsaeuren aus der reihe des resorcins", 1966, Archiu., vol 299, pp 545–559, (no translation).
Hartung, et al., "Palladium Catalyst, III, Reduction of Ketones", 1934, J. Am. Chem. Soc., vol. 56, pp 158–159.
Elsohly, et al., "Analogues of Poison Ivy Urushiol. Synthesis and Biological Activity of Disubstituted n–Alkybenzenes", 1986, J. Med.Chem., vol. 29 pp 606–611.
International Search Report, PCT/EP2004/006980, mailed on Dec. 22, 2004–3 pp.

* cited by examiner

Primary Examiner—Michael L. Shippen
(74) Attorney, Agent, or Firm—Ellen Plotkin

(57) ABSTRACT

A process for the preparation of a compound of formula I:

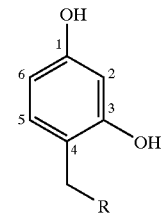

Figure 1:
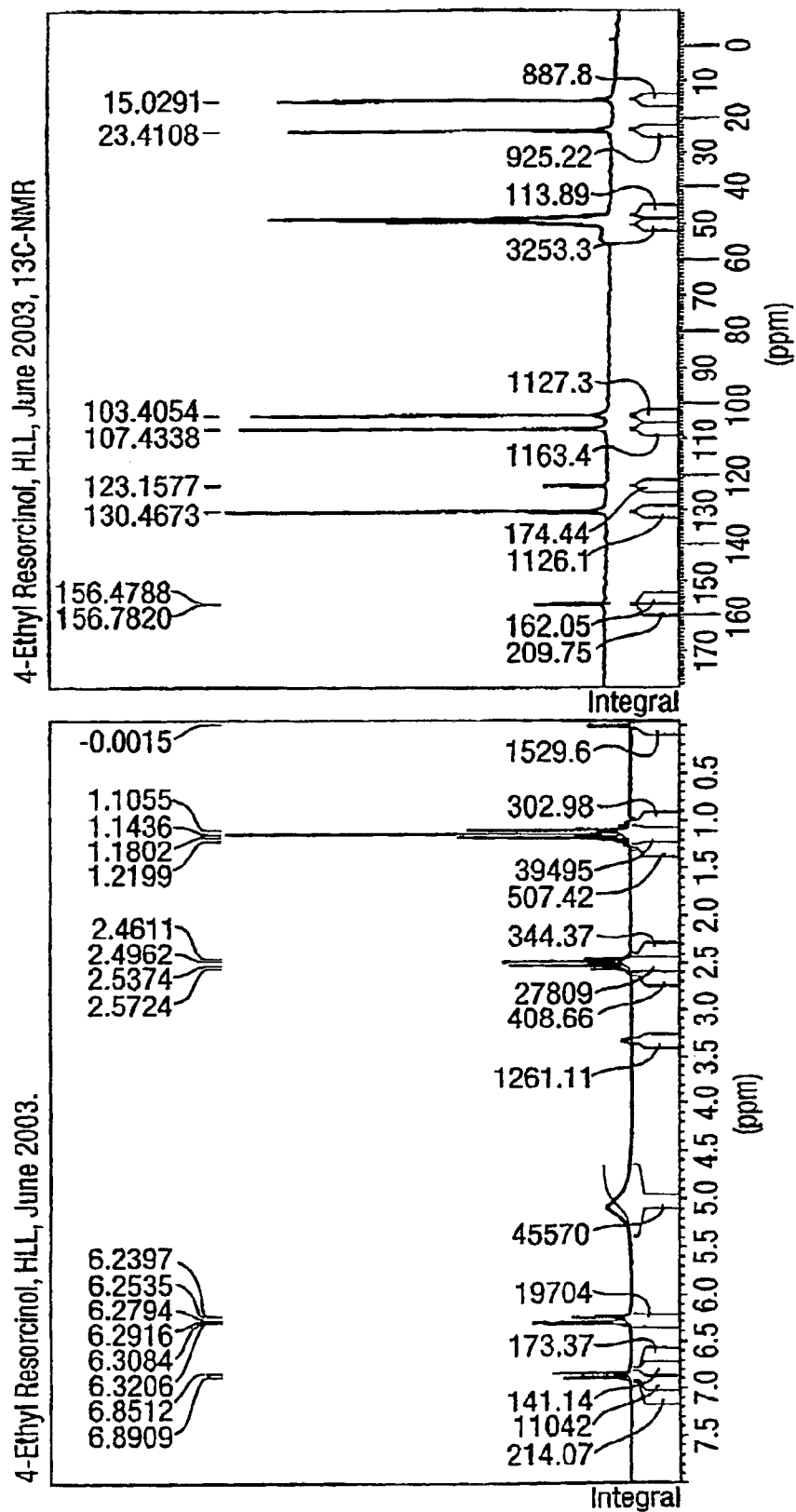

wherein R is a hydrogen or a $C_{1-6}$ alkyl group which is straight chain, branched or cyclic, with or without an oxygen, nitrogen or sulphur heteroatom anywhere in the chain or ring by reacting
a compound of formula II:

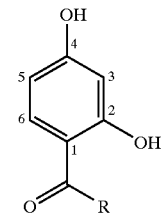

with a source of hydrogen selected from either hydrogen or water in the presence of a mixture of at least two catalysts selected from nickel, raney nickel, and palladium, at a pH below 7.0 in a solvent medium comprising an alcohol having a carbon chain length of up to 3.

11 Claims, 3 Drawing Sheets

PROCESS FOR THE PREPARATION OF A COSMETIC ACTIVE

TECHNICAL FIELD

The present invention relates to a novel process for the preparation of compounds of formula I in high yields and purity.

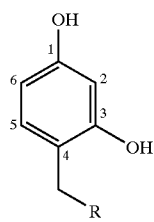

(FORMULA I)

Where R is hydrogen or an alkyl group having 1 to 6 carbon atoms which is either straight chain, branched or cyclic, with or without heteroatoms (oxygen, nitrogen or sulphur), anywhere in the chain or ring, starting with compounds of formula II.

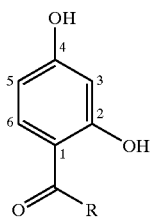

(FORMULA 11)

The invention is particularly useful for preparing compounds useful for preparation of cosmetic compositions.

BACKGROUND AND PRIOR ART

Resorcinol and its derivatives have a wide variety of applications. The largest consumption of resorcinol is in the tyre industry where the preferred hardening resins are based on resorcinol. Another value-added application of resorcinol and its derivatives is in cosmetic products. Some compounds like 2,4-dihydroxyacetophenone have been used in sun-protective applications or compositions for providing sun protection.

Alkyl and aryl resorcinols are reported to possess valuable therapeutic and antiseptic properties. In particular, 4-alkyl resorcinols are reported to have skin-beautifying effect and low toxicity and irritation when applied on to human skin. Alkyl resorcinols like 4-n-butyl resorcinol have been used in skin creams and lotions which are claimed to have good bleaching and anti-microbial effect. 2-alkyl resorcinols (where the alkyl group is linear) have been reported to have skin depigmentation properties.

Synthetic Communications 15 (14), 1315–24 (1985) describes a process to prepare 4-ethyl resorcinol by reaction of 2,4-dihydroxy acetophenone and sodium borocyano hydride in methanol medium. This process is difficult to implement on industrial scale and not cost-effective as sodium boro cyano hydride is not a catalyst but one of the reactants and so the reaction produces a lot of by products which are difficult to dispose off in an environmentally safe way.

There are many publications on the use of zinc and mercuric compounds to prepare compounds of formula I starting with compounds of formula II. J. Am Chem. Soc., 52, 4866–82 (1930) reports a process where 4-ethyl resorcinol has been prepared in 82% yield by reaction of 2,4-dihydroxy acetophenone with Zn and mercuric chloride in hydrochloric acid solution. Rec. trav. Chim. 50, 848–50 (1931) describes preparation of compound of formula I where R is a strain chain alkyl group with a carbon chain length of 5 in 84% yield by reaction of the corresponding ketone in the presence of Zn and dilute hydrochloric acid. The same product has been reported to be prepared in 71% yield in Acad. Rep. Populare Romine. Studii cercetari chim., 3, 13–18 (1955) by using Zn and mercuric chloride as the catalysts. The above methods are industrially not viable as the process comprises use of toxic and environmentally unfriendly chemicals containing mercury which are difficult to dispose off.

Tr. Tallin. Politekhn. In-ta (543) 78–83 (1983) reports the preparation of 4-ethyl resorcinol from 2,4-dihydroxyacetophenone in the presence of hydrochloric acid which is a non-catalytic reaction. The maximum yield reported is only 42% and therefore is not industrially workable.

Australian Journal of Chemistry, 22(3), 601–5 (1969) describes the preparation of 4-ethyl resorcinol by reaction of 2,4-dihydroxyacetophenone with sodium borohydride which is a non-catalytic reaction. This reaction is not an industrially feasible reaction due to the large amount of sodium borohydride that needs to be used and the problems of downstream purification.

Compound of formula I, but with a much higher carbon chain length of 14 has been reported in Journal of Medicinal Chemistry 29 (5), 606–11 (1986) to be prepared by the reaction of the corresponding compound of formula II with hydrogen gas and acetic acid using palladium as the catalyst in ethanol medium. This reaction produces the desired product with poor yield and the rate of reaction becomes increasingly slower with time.

J. Am Chem. Soc. (1939), 61, 249–54 describes that reduction of dihydroxy acetophenone with a palladium catalyst gave only a poor yield of 4-ethyl resorcinol and so the study was not extended.

There is thus a need felt in the art to develop a process to prepare compounds of formula I in high yields and purity, which can therefore be an industrially viable process. The present inventors have found that compounds of formula I can be prepared in very high yields and purity by reacting compounds of formula II with a source of hydrogen in the presence of a mixture of at least two catalysts chosen from Nickel, Raney Nickel and Palladium.

OBJECTS OF THE INVENTION

It is thus an object of the present invention to prepare compounds of the formula I, in high yields and purity.

It is a further object of the present invention to prepare compounds of formula I of high yields and purity in a single step reaction thus requiring only a single reaction vessel.

It is a further object of the present invention to prepare compounds of formula I, by using chemicals/raw materials which are readily available at economical price and are easily recycled for better economy.

It is a yet another object of the present invention to prepare compound of formula I that uses chemicals/raw materials which are readily available at economical price by a process that does not create by-products, which are difficult to separate or are environmentally unfriendly.

SUMMARY OF THE INVENTION

According to the basic aspect of the invention, there is provided a process for preparation of compound of formula I as hereinabove described, comprising reacting compound of formula II, as hereinabove described, with a source of hydrogen selected from either hydrogen or water in the presence of a mixture of at least two catalysts selected from nickel, raney nickel, and palladium, at a pH below 7.0 in a solvent medium comprising an alcohol having a carbon chain length of up to 3, such that palladium content is not greater than 10% by weight of the catalyst According to a preferred aspect of the invention there is provided a process for the preparation of compound of formula I as hereinabove described, comprising reacting compound of formula II, as herein above described, with hydrogen gas at pressures in the range of 300 to 750 psig, in the presence of at least two catalysts selected from nickel, raney nickel and palladium, at a pH below 7.0 in a solvent medium comprising an alcohol having a carbon chain length of up to 3, such that palladium content is not greater than 10% by weight of the catalyst.

According to a another preferred aspect of the invention there is provided a process for the preparation of compound of formula I as hereinabove described, comprising reacting compound of formula II, as hereinabove described, with water mixed with a solvent medium comprising alcohol having a carbon chain length of up to 3, in the presence of at least two catalysts selected from nickel, raney nickel and palladium, at a pH below 7.0, such that palladium content is not greater than 10% by weight of the catalyst.

It is particularly preferred that the reaction is carried out at a pH in the range of 4.0 to 7.0.

DETAILED DESCRIPTION OF THE INVENTION

The present invention provides for a novel process to prepare compounds of formula I, starting with compounds of formula II.

The compounds that correspond to the general formula I have the structure

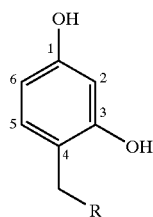

Where R is hydrogen or an alkyl group having 1 to 6 carbon atoms, which is either straight chain, branched or cyclic, with or without heteroatoms (oxygen, nitrogen or sulphur) anywhere in the chain or ring.

The process is a single step reaction which involves reacting compound of formula II, with a source of hydrogen selected from either hydrogen or water in the presence of a mixture of at least two catalysts selected from nickel, raney nickel, and palladium, at a pH below 7.0 in a solvent medium comprising an alcohol having a carbon chain length of up to 3, such that palladium content is not greater than 10% by weight of the catalyst.

The compounds that corresponds general formula II have the structure

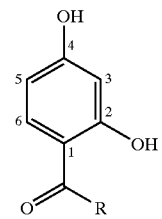

Where R is hydrogen or an alkyl group of 1 to 6 carbon atoms which is either straight chain, branched or cyclic, with or without heteroatoms like oxygen, nitrogen or sulphur anywhere in the chain or ring.

Although the raw materials, as per this invention are compounds that correspond to general formula II, the process could also be carried out starting with precursors of compounds of general formula II, from which reactions well known in the art could be employed to first prepare compounds of formula II, following which the process of the invention could be carried out.

The reaction is essentially carried out in the presence of two or more catalysts selected from nickel, raney nickel and palladium. The nickel catalyst may be used as such or may be supported, for example on silica. It is preferred, that when palladium is used, the palladium is in the form of palladium on carbon. When nickel and raney nickel are two catalysts used, they could be used in any ratio. When palladium is one of the catalysts, palladium is present in the range of 0.01% to 10% by weight of the catalysts, more preferably at 0.01 to 2% by weight of the catalysts, most preferably at 0.01 to 1% by weight of the catalysts. The catalysts are used in the range of 0.1 to 40% by weight of the compounds of formula II, more preferably in the range of 5 to 30% by weight of the compounds of formula II.

The source of hydrogen is either hydrogen or water. When hydrogen is used as the source of hydrogen, the preferred range of hydrogen pressure is from 150 to 750 psig. Water may also be used as the source of hydrogen. When water is used at greater than 50 weight % of the solvent medium, the reaction can be carried out at atmospheric pressure. It is possible to carry out the process as per the invention with a solvent medium comprising up to 75% water.

The reaction is carried out in a solvent medium comprising alcohol with carbon chain lengths of up to 3. The solvent medium may comprise solvents other than alcohol and such preferred solvents are 1,2-dichloroethane and tetrahydrofuran. The alcohol that is used may be of 100% purity or may include water/moisture. It is not essential that all of the compounds of formula II dissolve in the solvent medium. When water is the source of hydrogen, the water may be mixed with the solvent medium. The alcohol is preferably methanol, ethanol or isopropyl alcohol. The reaction is carried out at a pH below 7.0, preferably in the range of 4.0 to 7.0. Acidic materials may be used to achieve the pH of the reaction medium. The acidic materials that may be used include methane sulfonic acid, sulfuric acid, hydrochloric acid, phosphoric acid, p-toluene sulfonic acid, acetic acid, zinc chloride and acidic ion-exchange resins such as Amberlyst (available from Rohm & Hass), and Dowex (from Dow chemicals). One or more of the acids can be used in the reaction.

The reaction as per this invention is preferably carried out from 20 to 80° C.

At the end of the reaction, the desired product may be purified by separation of the solvent using any known method of separation. The preferred method of separation of the desired products from the solvent is by distillation of the solvent followed by filtration of the catalyst. When the solvent medium contains water and alcohol, the alcohol is separated by distillation at the end of the reaction. The product is soluble in the balance water while the unreacted reactants of compounds of formula I is insoluble in water which may then be separated and recycled for further reaction.

The invention will now be illustrated with the help of the following non-limiting examples:

EXAMPLES
Methods and Materials:
Gas Chromatography/mass Spectroscopy (GC-MS):

GC-MS was performed on a Finigen MAT mass spectrophotometer with A200S Autosampler Series Plus gas chromatrograph in conjunction with a GCQ 2.0 MS/MS Software. A DB-1 column (60 meter) was used.
Gas Chromatography (GC):

GC was performed on a Chemito 2000 Gas chromatographer (flame ionization) using a BP1 capillary column (30 meter×0.25 mm). The injection temperature was set at 250 C.
Infrared (IR)

IR spectra were recorded on a Shimutzu FT-IR-8101A spectrometer using NaCl cell. Peak positions are listed in cm-1 as vs (very strong), s (strong), m (medium), w (weak) or br (broad).
Proton Magnetic Resonance (NMR):

NMR spectra were recorded on a Bruker 200 MHZ instrument. Chemical shifts are reported in parts per million from tetramethanesilane as an internal standard. Spin multiplicities are indicated as follows: s (singlet), d (doublet), t (triplet), m (multiplet) and br (broad). The deuterated NMR solvents contain 99.00–99.9% deuterium in the indicated position.

All solvents were reagent grade and were used as received. All reagents were purchased from Aldrich or Sigma Chemical Companies and were used as received unless otherwise noted.

Example 1

To a hydrogenation reactor (1 liter) was added 76 g of 2,4-dihydroxy acetophenone (0.5 moles), methanol (300 ml) and 7.6 g of Raney Nickel (type F—From Kallin). The reactor was purged with nitrogen several times. The hydrogen pressure was adjusted to 500 psi and the reaction mixture was heated to 75–80° C. fo up to 12 hrs. The dark brown reaction mixture (pH>8.0) was cooled to room temperature and filtered. The solvent was removed on a rotavap (below 60° C.) and the thick liquid brown residue was characterized by GC, NMR and Mass spectroscopy. The spectroscopic data indicated that 4-ethyl resorcinol is formed at low yields (<30%) along with several by-products including the dimers of 2,4-dihydroxy acetophenone.

Example 2

To a hydrogenation reactor (1 liter) was added 76 g of 2,4-dihydroxy acetophenone (0.5 moles), methanol (300 ml) and 15.2 g of Raney Nickel (type F—From Kallin at pH of 8 to 9). The reactor was purged with nitrogen several times. The hydrogen pressure was adjusted to 400 psi and the reaction mixture was heated at 75–80 C. up to 10 hrs. The reaction mixture (pH>8.0) was cooled to room temperature and filtered. The solvent was removed on a rotavap (below 60 C.) and the thick brown residue was characterized by GC, NMR and Mass spectroscopy. The spectroscopic data indicated that ethyl resorcinol is formed at low yields (<30%) along with several by-products including the dimers of 2,4-dihydroxy acetophenone.

Example 3

2,4-dihydroxy acetophenone (76 g, 0.5 mole) was charged in a 1 liter autoclave reactor along with methanol (300 ml), and Raney Nickel (15.2 g—washed several times with water and water/methanol to a pH of 7.0) and 750 mg of Pd/C. The autoclave was checked for leaks with 100–200 psi of nitrogen. The autoclave was pressurized to 300 psi with hydrogen and stirred at 70° C. for 8 hrs. During this time 95% of the theoretical value for hydrogen was consumed. The reaction was vented and the contents were filtered through a milipore filter to give a light yellow solution. Concentration of this solution in vacuo gave a solid. This solid was crystalized from 1,2-dichloroethane to give 4-ethyl resorcinol in 70% isolated yield. The unreacted 2,4-dihydroxy acetophenone was recovered (~27%) from the reaction mixture and was recycled. The structure of 4-ethyl resorcinol was characterized by using the NMR, Gas Chromatography, IR and Mass spectroscopy.

Example 4

Figure 2:
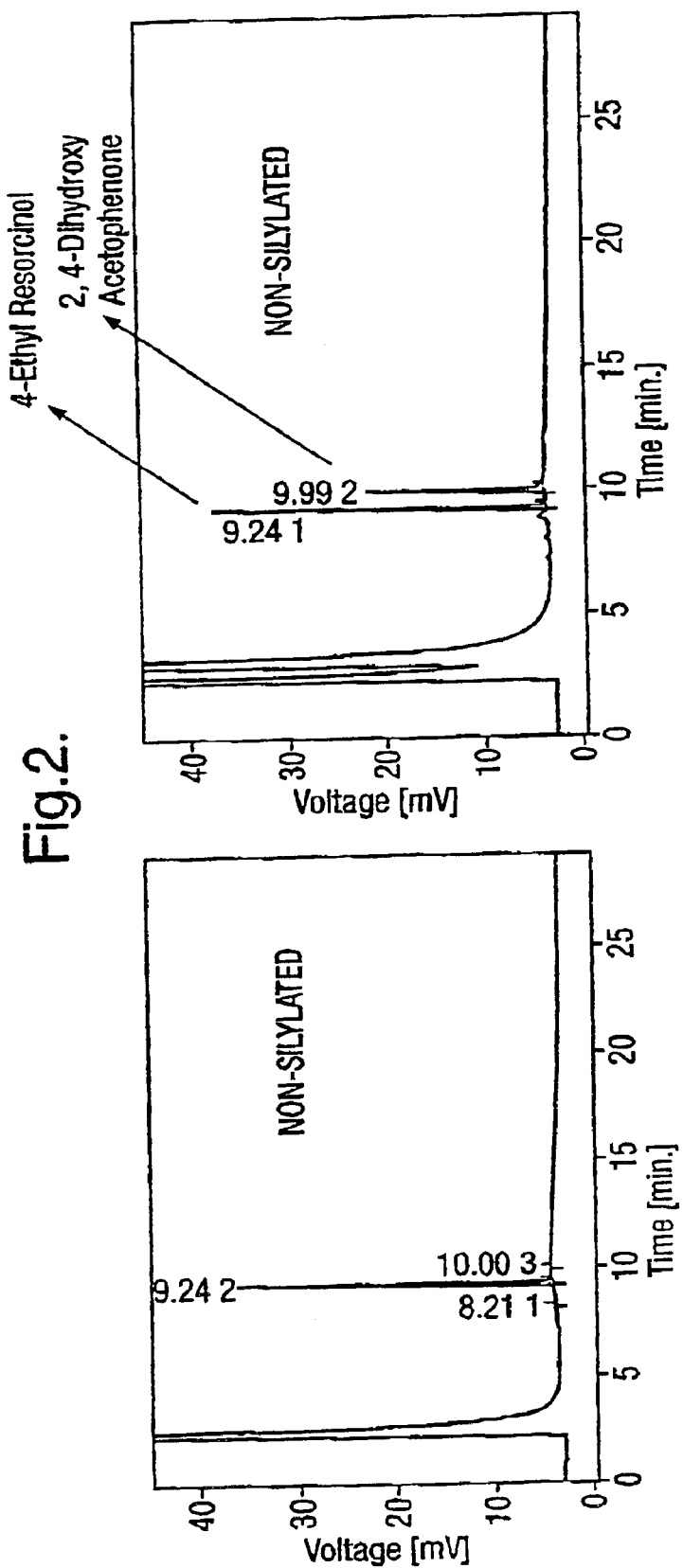
Figure 3:
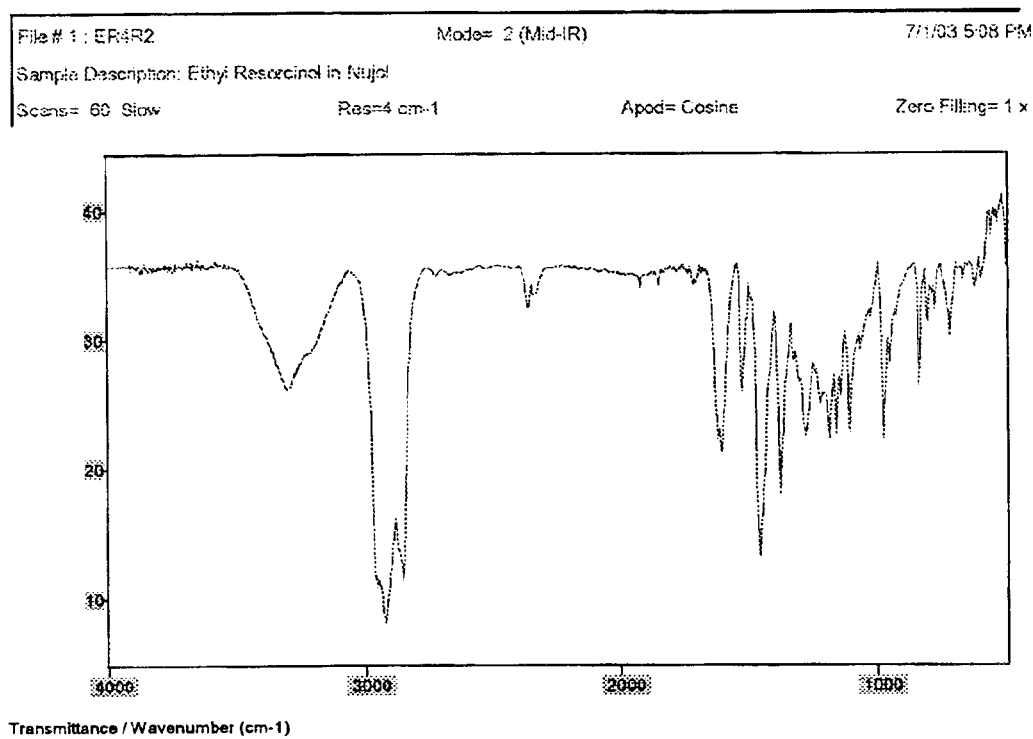

2,4-Dihydroxy acetophenone (76 g, 0.5 mole) was charged in a 1 liter autoclave reactor along with methanol (300 ml), acetic acid (5 ml), and Raney Nickel (15.2 g washed several times with water and water/methanol) and 750 mg of Pd/C. The pH of the system was 5.0. The autoclave was checked for leaks with nitrogen. The autoclave was pressurized to 500 psi with hydrogen and stirred at 70–75° C. up to 8 hrs. During this time 97% of the theoretical value for hydrogen was consumed. The reaction was vented and the contents were filtered through a milipore filter to give a yellow solution. Concentration of this solution in vacuo gave a solid. This solid was crystalized from 1,2-dichloroethane to give 4-ethyl resorcinol in 85% isolated yield. The unreacted 2,4-dihydroxy acetophenone was recovered (~13%) from the reaction mixture and was recycled. The structure of 4-ethyl resorcinol and 2,4-dihydroxy acetophenone were characterized by NMR (see FIG. 1), Gas Chromatography (see FIG. 2), IR (See FIG. 3) and Mass spectroscopy. The mass spectroscopy indicated that the mass was 138.

Example 5

In a three necked round bottom flask (equipped with a condensor, additional funnel and mechanical stirrer) was added 15.2 g of a combination of Raney Nickel and Ni supported on silica. (50:50). 100 ml of a mixture of 50:50 ethanol:water was added and the reaction was heated at reflux conditions. 15.2 g of 2,4-dihydroxy acetophenone in 100 ml of water:ethanol and 10 ml of acetic acid was placed in the additional funnel and slowly added to the mixture (dropwise). The reaction was filtered through a milipore filter to give a pale yellow solution. Concentration of this solution in vacuo gave a solid. This solid was crystalized from 1,2-dichloroethane to give 4-ethyl resorcinol in 80% isolated yield. The unreacted 2,4-dihydroxy acetophenone was recovered (~17%) form the reaction mixture and was recycled. The structure of 4-ethyl resorcinol and 2,4-dihydroxy acetophenone were characterized by NMR, Gas Chromatography, IR and Mass spectroscopy Examples 6 to 16

The conditions under which examples 6 to 16 were carried out are summarized in Table-1. The procedure under which these experiments were carried out are also given in the table-1 and these procedures are given below as procedure 1 and procedure 2.

Procedure 1

To a hydrogenation reactor (1 liter) is added 2,4-dihydroxy acetophenone, alcohol (300 ml) and the catalyst or the combination of the catalysts. The reactor is purged with nitrogen. The hydrogen pressure is adjusted to 100–500 psi and the reaction mixture is heated to 70–80° C. for up to 12 hrs. The catalyst is filtered and the solvent is removed using a rotavap (below 60° C.). The residue is characterized by GC, NMR and Mass spectroscopy.

Procedure 2

In a three necked round bottom flask (equipped with a condenser, additional funnel and mechanical stirrer) was added the catalyst or combination of the catalysts. 100 ml of a mixture of 50:50 ethanol:water was added and the reaction was heated to reflux conditions. 2,4-dihydroxy acetophenone in 100 ml of water:ethanol mixture with or without acids was placed in the additional funnel and was added to the mixture (dropwise-2–4 hrs). The reaction was filtered through a milipore filter and concentrated in vacuo to give a solid. This solid was crystalized from 1,2-dichloroethane to give 4-ethyl resorcinol. The unreacted 2,4-dihydroxy acetophenone is recovered from the media and recycled. The structure of 4-ethyl resorcinol and 2,4-dihydroxy acetophenone were characterized by NMR, Gas Chromatography, IR and Mass spectroscopy

TABLE 1

| Example No | Procedure No. | 2,4-dihydroxy acetophenone quantity) | Amount (g) and type of Catalyst | pH | Temperature (° C.) | Hydrogen Pressure (psi) | Reaction time (hours) | 4-Ethyl resorcinol (Yield) |
|---|---|---|---|---|---|---|---|---|
| 6 | 1 | 76 g | 22.8 g of Raney Ni | ~8.5 | 75–80 | 300 | 3–10 | ~10% |
| 7 | 1 | 76 g | 22 g Ni on Silica | ~8.0 | 75–80 | 500 | 3–12 | ~30% |
| 8 | 1 | 76 g | 22.5 g Ni on Silica and Raney Ni(50:50) | ~8.5 | 70–80 | 300–500 | 2–10 | ~10–30% |
| 9 | 1 | 76 g | 7.6 g Pd/C | ~7.5 | 70–80 | 400 | 8 | ~10% |
| 10 | 1 | 76 g | 22.8 g (Raney Ni | ~7.00 | 70–80 | 500 | 6–10 | 45–50% |
| 11 | 1 | 76 g | 21.8 g Raney Ni and Ni on Silica (50:50) and 5 ml acetic Acid | ~5 | 70–80 | 500 | 8 | 75% |
| 12 | 2 | 76 g | 22.0 g Raney Ni and Ni on Silica | 7.00 | Reflux | 14.7 psi | 3–10 | 70–90 |
| 13 | 2 | 14.5 g | 28.90 g Raney Ni and Ni on Silica (50:50) and 5 ml acetic Acid | 5.00 | reflux | 14.7 (atmospheric) | 2–10 | 79–92 |
| 14 | 1 | 76 g | 22.0 g Raney Ni and Pd/C (95:5) | 7.0 | 70 | 300–500 | 3–8 | 75–90% |
| 15 | 1 | 76 g | 22.5 g Raney Ni and Ni on Silica (50:50) | 7.0 | 75 | 300–500 | 3–12 | 70–90% |
| 16 | 1 | 76 g | 21.0 g Raney Ni and Ni on silica and Pd/C (50:45:5) | 6.50 | 70 | 200–400 | 2–8 | 65–92% |

The examples 3 to 5 and examples 11 to 16 demonstrate that compounds of formula I can be prepared in high yield using the process as per the invention.

What is claimed is:

1. A process for the preparation of a compound of formula I:

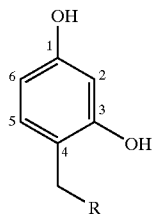

wherein R is a hydrogen or a $C_{1-6}$ alkyl group which is straight chain, branched or cyclic, with or without an oxygen, nitrogen or sulphur heteroatom anywhere in the chain or ring by reacting
a compound of formula II:

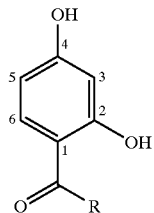

with a source of hydrogen selected from either hydrogen or water in the presence of a mixture of at least two catalysts selected from nickel, raney nickel, and palladium, at a pH below 7.0 in a solvent medium comprising an alcohol having a carbon chain length of up to 3.

2. The process of claim 1 wherein the palladium content is not greater than 10% by weight of the catalyst.

3. The process of claim 1 wherein the palladium content is in the range 0.01% to 1% by weight of the catalyst.

4. The process of claim 1 wherein the source of hydrogen is hydrogen gas at pressures in the range of 300 to 750 psig.

5. The process of claim 1 wherein the source of hydrogen is water.

6. The process of claim 1 wherein the solvent medium is up to 75% water.

7. The process of claim 1 wherein the reaction is carried out at a pH in the range 4.0 to 7.0.

8. The process of claim 1 wherein the catalysts are used in the range 5% to 30% by weight of the compounds of formula II.

9. The process of claim 1 wherein the reaction is carried out at from 20 to 80° C.

10. The process of claim 1 wherein the palladium is in the form of palladium on carbon.

11. The process of claim 1 comprising the additional first step of reacting a precursor of the compound of formula II to prepare a compound of formula II.

* * * * *